US010492743B2

(12) United States Patent
Kim et al.

(10) Patent No.: US 10,492,743 B2
(45) Date of Patent: Dec. 3, 2019

(54) X-RAY IMAGING APPARATUS HAVING FUNCTION OF GENERATING THREE-DIMENSIONAL SURFACE DATA AND PHOTOGRAPHING METHOD THEREOF

(71) Applicants: VATECH Co., Ltd., Gyeonggi-do (KR); VATECH EWOO Holdings Co., Ltd., Gyeonggi-do (KR)

(72) Inventors: Keun Yeoung Kim, Gyeonggi-do (KR); Taewoo Kim, Gyeonggi-do (KR); Youn Joo Yang, Gyeonggi-do (KR); Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 99 days.

(21) Appl. No.: 15/756,572

(22) PCT Filed: Aug. 29, 2016

(86) PCT No.: PCT/KR2016/009565
§ 371 (c)(1),
(2) Date: Feb. 28, 2018

(87) PCT Pub. No.: WO2017/039253
PCT Pub. Date: Mar. 9, 2017

(65) Prior Publication Data
US 2018/0338735 A1    Nov. 29, 2018

(30) Foreign Application Priority Data

Aug. 28, 2015    (KR) .................... 10-2015-0121426

(51) Int. Cl.
*A61B 6/14*    (2006.01)
*A61B 6/00*    (2006.01)
(Continued)

(52) U.S. Cl.
CPC .................. *A61B 6/14* (2013.01); *A61B 6/00* (2013.01); *A61B 6/03* (2013.01); *A61B 6/032* (2013.01);
(Continued)

(58) Field of Classification Search
None
See application file for complete search history.

(56) References Cited

U.S. PATENT DOCUMENTS 8,634,631 B2 *    1/2014    Kanerva .................. A61B 6/03
                                                          382/132
2003/0129565 A1    7/2003    Kaza
(Continued)

FOREIGN PATENT DOCUMENTS

KR    10-2010-0070822 A    6/2010
KR    10-2011-0020323 A    3/2011
(Continued)

OTHER PUBLICATIONS

European Patent Office, Extended European Search Report of corresponding EP Patent Application No. 16842219.4, dated Mar. 22, 2019.

*Primary Examiner* — Hoon K Song
(74) *Attorney, Agent, or Firm* — IP Legal Services, LLC

(57) ABSTRACT

Disclosed are an X-ray imaging apparatus capable of acquiring highly accurate three-dimensional surface data as well as a CT image of teeth and surrounding tissues thereof of a subject without increasing the dose of X-ray and the discomfort for the subject compared to conventional CT imaging, and an X-ray imaging method using the same. The X-ray imaging apparatus includes an X-ray generator; an X-ray sensor disposed to face the X-ray generator, and configured to receive X-rays transmitted through a subject to generate an electric signal, and a subject jig configured to support the subject and to move the subject to be relatively (Continued)

rotated about at least two axes with respect to an X-ray propagation path, wherein a CT image and high-precision three-dimensional surface data are reconstructed and provided by using a plurality of X-ray imaging data acquired through a plurality of scan sequences.

4 Claims, 5 Drawing Sheets

(51) Int. Cl.
*A61B 6/03* (2006.01)
*A61C 7/00* (2006.01)
*G01N 23/046* (2018.01)
*G06T 3/40* (2006.01)
*G06T 11/00* (2006.01)
*A61C 13/00* (2006.01)
*A61B 8/08* (2006.01)
*G01V 5/00* (2006.01)

(52) U.S. Cl.
CPC .......... *A61B 6/4452* (2013.01); *A61B 6/5241* (2013.01); *A61C 7/002* (2013.01); *G01N 23/046* (2013.01); *G06T 3/4069* (2013.01); *G06T 11/006* (2013.01); *A61B 6/488* (2013.01); *A61B 8/5269* (2013.01); *A61C 13/0004* (2013.01); *G01N 2223/309* (2013.01); *G01N 2223/3307* (2013.01); *G01N 2223/612* (2013.01); *G01V 5/005* (2013.01)

(56) References Cited

U.S. PATENT DOCUMENTS

| | | |
|---|---|---|
| 2004/0191719 A1 | 9/2004 | Kaza |
| 2007/0092850 A1 | 4/2007 | Kaza |
| 2007/0196009 A1 | 8/2007 | Deinzer |
| 2012/0069958 A1* | 3/2012 | Wang ................ A61B 5/0073 378/21 |
| 2012/0321033 A1* | 12/2012 | Stearns ............. G01N 21/763 378/4 |
| 2016/0047759 A1 | 2/2016 | Wang et al. |

FOREIGN PATENT DOCUMENTS

| | | |
|---|---|---|
| KR | 10-1092907 B1 | 12/2011 |
| KR | 10-1242629 B1 | 3/2013 |
| KR | 10-2014-0044158 A | 4/2014 |
| KR | 10-2015-0083338 A | 7/2015 |
| WO | 2014/168796 A1 | 10/2014 |

* cited by examiner

X-RAY IMAGING APPARATUS HAVING FUNCTION OF GENERATING THREE-DIMENSIONAL SURFACE DATA AND PHOTOGRAPHING METHOD THEREOF

CROSS REFERENCE TO RELATED APPLICATIONS

This application is a National Stage Patent Application of PCT International Patent Application No. PCT/KR2016/009565 (filed on Aug. 29, 2016) under 35 U.S.C. § 371, which claims priority to Korean Patent Application No. 10-2015-0121426 (filed on Aug. 28, 2015), the teachings of which are incorporated herein in their entireties by reference.

TECHNICAL FIELD

The present invention relates generally to an X-ray imaging apparatus and an X-ray imaging method using the same. More particularly, the present invention relates to a dental CT (computed tomography) imaging apparatus using X-rays and an imaging method using the same which are mainly used for dental diagnosis and prosthesis manufacturing.

BACKGROUND ART

Generally, a process of manufacturing a dental prosthesis in a dental clinic includes removing a damaged tooth, obtaining an engraved dental model by taking an impression of a removed tooth and surrounding oral tissues using an impression material, casting an embossed tooth model by injecting plaster into the engraved dental model, obtaining digital three-dimensional surface data is obtained through 3D scanning and surface rendering of the embossed dental model, and designing the prosthesis using CAD/CAM system and processing appropriate material according to its surface coordinates.

However, of the above processes, there is a possibility that errors in actual teeth may occur during the process of taking the impression, the process of obtaining engraved and embossed dental models based on the impression, or the process of scanning the dental model. The surface coordinate data used to manufacture the final prosthesis is obtained from the dental model, not the actual tooth, wherein the volume data of the actual teeth is obtained mainly through the dental X-ray imaging apparatus, whereas the surface data of the dental model is obtained through a separate scanning device, so data verification is difficult.

For this reason, as disclosed in the documents of Korean Patent Application Publication No. 10-2011-0020323 and Korean Patent Application Publication No. 10-2010-0070822, an attempt was made to acquire a surface image of a tooth from an X-ray image of a subject's teeth directly imaged by using a dental X-ray imaging apparatus and utilize it in the manufacture of a prosthesis. However, in order to obtain a suitable level of image for the CAD/CAM system, the X-ray imaging time becomes long, which causes a problem of increasing the radiation dose. The quality of the imaged image may be deteriorated or error may occur due to the movement or vibration of the subject during the imaging time.

Meanwhile, an intraoral scanner is also used to directly acquire three-dimensional surface data of the patient's intraoral structure. However, the intraoral scanner requires not only two or more skilled radiographers but also the inconvenience that the patient has to open his mouth for a long time. Further, it is problematic in that due to the limitation of the intraoral scanner using the reflected signal, the accuracy of the data for critical areas, such as the interdental area or gingival boundaries, in the treatment plan is reduced.

DISCLOSURE

Technical Problem

Accordingly, the present invention has been made keeping in mind the above problems occurring in the related art, and one object of the present invention is to provide an X-ray imaging apparatus and an X-ray imaging method using the same, in which compared to the conventional CT imaging, CT images of the subject's teeth and surrounding tissues, as well as highly accurate three-dimensional surface data, can be obtained without increasing the dose of X-ray and discomfort for the subject. Further, another object of the present invention is to provide an X-ray imaging apparatus and an X-ray imaging method using the same, in which three-dimensional surface data of the impression body taken from the subject's teeth and surrounding tissues can be provided with the level of precision that CAD/CAM operation is possible, without a separate impression body scanner.

Technical Solution

In order to achieve the above object, according to some aspects of the present invention, there is provided an X-ray imaging apparatus including: an X-ray generator configured to irradiate X-rays; an X-ray sensor disposed to face the X-ray generator, and configured to receive X-rays transmitted through a subject to generate an electric signal; and a subject jig configured to support the subject and to move the subject to be relatively rotated about at least two axes with respect to an X-ray propagation path between the X-ray generator and the X-ray sensor, wherein three-dimensional surface data of the subject is reconstructed by using a plurality of X-ray imaging data acquired through both a first scan sequence in which the subject is relatively rotated about a first axis with respect to the X-ray propagation path, and a second scan sequence in which the subject is rotated a second axis different from the first axis to change a direction and is relatively rotated again about the first axis.

The subject jig may be configured to be relatively rotatable about three different axes with respect to the X-ray propagation path, and the plurality of X-ray imaging data may be acquired through first to third scan sequences in which the subject is relatively rotated respectively about the three different axes with respect to the X-ray propagation path.

According to some aspects of the present invention, there is provided an X-ray imaging method including: mounting an impression body of an oral structure of a subject to a subject jig having a rotatable impression body-mounting member; performing a first scan sequence to relatively rotate the impression body about a first axis with respect to a X-ray propagation path; changing a direction of the impression body by rotating the impression body-mounting member about a second axis different from the first axis; performing a second scan sequence to relatively rotate the impression body again about the first axis with respect to the X-ray propagation path; and reconstructing three-dimensional surface data of the impression body by using a plurality of X-ray imaging data acquired through both the first scan sequence and the second scan sequence.

According to some aspects of the present invention, there is provided an X-ray imaging apparatus including: an X-ray generator configured to irradiate X-rays; an X-ray sensor including a plurality of pixels, the X-ray sensor disposed to face the X-ray generator, and configured to receive X-rays transmitted through a subject to generate an electric signal; and a subject jig configured to support the subject and to move the subject to be relatively rotated about at least one axis with respect to an X-ray propagation path between the X-ray generator and the X-ray sensor, wherein three-dimensional surface data of the subject is reconstructed by using a plurality of X-ray imaging data acquired through both a first scan sequence in which the subject is relatively rotated about a first axis with respect to the X-ray propagation path, and a second scan sequence in which the X-ray sensor is relatively rotated again about the first axis in a state where the X-ray sensor is offset by a distance smaller than a width of one pixel in a direction crossing the X-ray propagation path.

The X-ray sensor may be offset by 1/M (where M is a natural number equal to or greater than 2) of the width of the pixel for each scan sequence, and the three-dimensional surface data of the subject may be reconstructed by using the plurality of X-ray imaging data acquired through first to Mth scan sequences.

According to some aspects of the present invention, there is provided an X-ray imaging method including: mounting an impression body of an oral structure of a subject to a subject jig having a rotatable impression body-mounting member; performing a first scan sequence to relatively rotate the impression body about a first axis with respect to a X-ray propagation path; offsetting an X-ray sensor by a distance smaller than a width of one pixel in a direction crossing an X-ray propagation path; performing a second scan sequence to relatively rotate the impression body again about the first axis with respect to the X-ray propagation path; and reconstructing three-dimensional surface data of the impression body by using a plurality of X-ray imaging data acquired through both the first scan sequence and the second scan sequence.

The X-ray sensor may be offset by 1/M (where M is a natural number equal to or greater than 2) of the width of the pixel for each scan sequence, and the three-dimensional surface data of the subject may be reconstructed by using the plurality of X-ray imaging data acquired through first to Mth scan sequences.

According to some aspects of the present invention, there is provided an X-ray imaging method including: applying an X-ray scanning aid with a CT number different from intraoral soft tissues onto an oral structure of a subject to cover the same; performing a scan sequence by rotating an X-ray generator and an X-ray sensor disposed to face each other around the oral structure of the subject; and reconstructing a CT image and three-dimensional surface data of the oral structure of the subject by using a plurality of X-ray imaging data acquired through the scan sequence.

Advantageous Effects

According to the present invention configured as describe above, an X-ray imaging apparatus and an X-ray imaging method using the same are advantageous in that it is possible to obtain CT images of the subject's teeth and surrounding tissues, as well as highly accurate three-dimensional surface data, without increasing the dose of X-ray and discomfort for the subject compared to the conventional CT imaging. Further, it is possible to provide complementary and verifiable data between CT reconstruction data and three-dimensional surface data on tomography and volume, thus providing more accurate three-dimensional surface data, and particularly, it is possible to provide much more accurate data for interdental area or gingival boundaries compared to the conventional one. Further, it is possible to provide three-dimensional surface data of the impression body taken from the subject's teeth and surrounding tissues with the level of precision that CAD/CAM operation is possible, without a separate impression body scanner.

MODE FOR INVENTION

Figure 1:
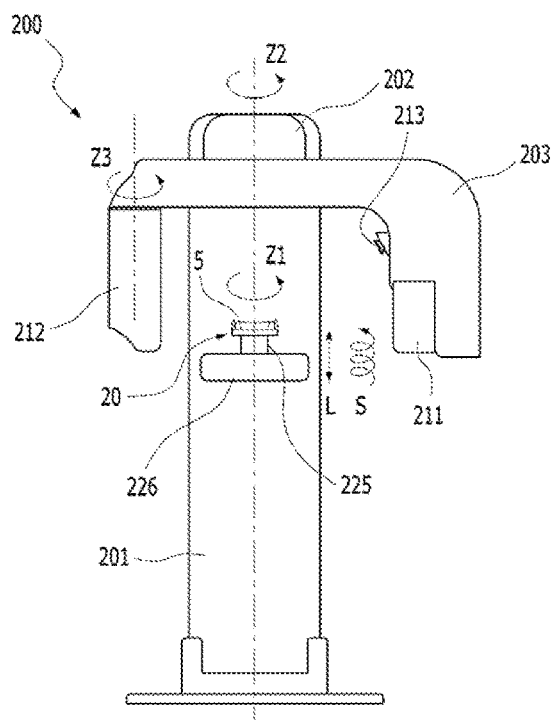
FIG. 1 shows an X-ray imaging apparatus according to an embodiment of the present invention.

Hereinafter, various embodiments of the present invention will be described with reference to the accompanying drawings. The technical idea of the present invention will be understood more clearly by the embodiments. The present invention is not limited to the embodiments described hereinbelow. The same reference numerals are used to designate the same or similar components, and a description of components having the same reference numerals as those described in any one of the drawings may be omitted.

FIG. 1 shows an X-ray imaging apparatus according to an embodiment of the present invention.

An X-ray imaging apparatus according to the present invention, like a conventional dental X-ray imaging apparatus, includes a column portion 201, a rotation arm 203, and a rotation a arm-connection portion 202 connecting the column portion and the rotation arm. The rotation arm 203 is configured such that an X-ray generator 211 and an X-ray sensor 212 are disposed at opposite ends of the rotation arm to face each other, and the rotation a arm-connection portion 202 is configured such that a first end thereof is mounted to the column portion 201 and a second end thereof is connected to a Z2-axis that is a rotation axis of the rotation arm 203. Herein, the X-ray sensor 212 may be a dental panoramic imaging sensor close to a linear shape with a large aspect ratio of the incidence surface, a CT imaging sensor in the form of a surface sensor having a relatively small aspect ratio, or a cephalometric imaging sensor. As in the embodiment, a universal dental X-ray imaging apparatus 200 is configured such that the panoramic imaging sensor and the CT imaging sensor are disposed at opposite sides of one body to be rotatable about a Z3-axis shown in the drawing, so the two sensors may be selectively used.

The X-ray imaging apparatus 200 according to the embodiment may include a subject jig 225 provided at the column portion 201. The subject jig 225 may be, for example, three-axis rotatable, but fundamentally, is disposed between the X-ray generator 211 and the X-ray sensor 212 under the rotation arm 203 to be rotatable about a Z1-axis parallel to the rotation axis of the rotation arm 203. The subject jig 225 is disposed on a jig base 226 that is at least temporarily mounted to the column portion 201, and may include an impression body-mounting member 20 configured to directly mount and support an impression body 5, that is, a dental model of an oral structure, such as teeth of a subject. The jig base 226 may also serve as a support for the jaw of the subject during general panoramic and CT imaging.

The impression body-mounting member 20 may move in a substantially vertical direction with respect to the X-ray propagation path, as indicated by the arrow L. In other words, the impression body-mounting member may perform a vertical linear movement between the X-ray generator 211 and the X-ray sensor 212. Further, the impression body-mounting member 20 may perform a helical movement in the same shape as the arrow S by simultaneously performing the rotational movement and the linear movement described above. Herein, the rotation, linear or helical movement of the impression body-mounting member 20 may be relative to the jig base 226 mounted to the column portion 201.

Herein, the rotation center Z1-axis of the impression body-mounting member 20 may be the same as or different from the rotation center Z2-axis of the rotation arm 203. If Z1 and Z2 are equal, the impression body-mounting member 20 is rotated about one axis with respect to the X-ray propagation path. On the other hand, if the directions of Z1 and Z2 are different, by individually or simultaneously rotating the rotation arm 203 and the impression body-mounting member 20, the impression body-mounting member 20 may have the same effect as being rotated about two axes with respect to the X-ray propagation path.

When the X-ray imaging apparatus according to the embodiment is used to acquire surface data of the impression body 5, the impression body 5 is mounted to the impression body-mounting member 20, and a scan sequence may be performed to image multiple X-ray transmission images by rotating the rotation arm 203, or a scan sequence may be performed by rotating the subject jig 225 or the impression body-mounting member 20 instead of moving the rotation arm 203. Herein, the scan sequence is a series of imaging processes of obtaining a plurality of X-ray imaging data necessary for reconstruction of a basic CT image or three-dimensional surface data over the subject's imaging area. When a non-living subject, such as an impression body 5, is imaged, since it is relatively free from radiation exposure limitations, it is possible to repeat the scan sequence several times in order to obtain high-precision surface data. Methods for obtaining high-precision surface data will be described in more detail hereinbelow.

Meanwhile, the X-ray imaging apparatus 200 according to the embodiment may further include an optical camera 213 imaging an optical image of the subject provided at at least two locations. The optical camera 213 is disposed, for example, on one side of the rotation arm 203 so that the optical image of the surface of the subject can be imaged at various angles in the above described scan sequence or in a separate imaging sequence. The optical image of the surface of the subject imaged at the optical camera 213 may be reconstructed along with a plurality of X-ray imaging data and utilized to provide a three-dimensional surface image. In other words, the X-ray imaging apparatus 200 according to the embodiment can provide an accurate and realistic three-dimensional surface image by synthesizing an optical image of a surface imaged by an optical camera on the surface of an X-ray CT three-dimensional image including information on the three-dimensional outline of the surface.

Figure 2:
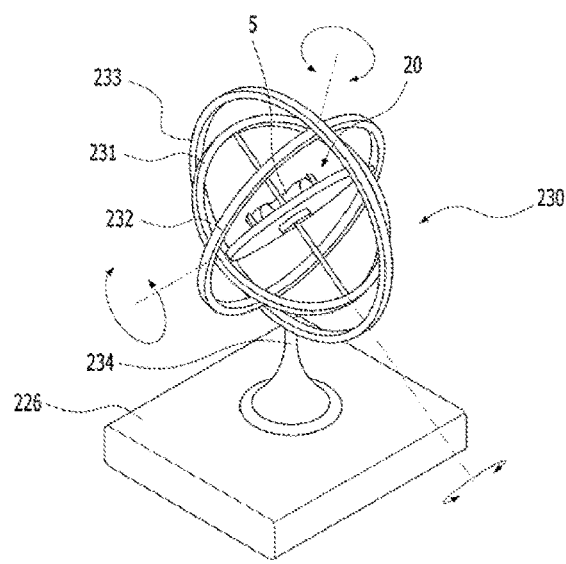
FIG. 2 roughly shows an example of a three-axis rotating subject jig applicable to the embodiment of FIG. 1.

FIG. 2 roughly shows an example of a three-axis rotating subject jig applicable to the embodiment of FIG. 1.

A three-axis rotating subject jig 230 shown in the drawing may be placed on the jig base 226 in place of the subject jig 225 of FIG. 1. However, not limited thereto, the three-axis rotating subject jig may be provided at the column portion 201 or a lower portion of the rotation arm 203 of FIG. 1. The three-axis rotating subject jig may be fixedly attached to the ground by a separate supporting structure.

The three-axis rotating subject jig 230 according to the embodiment has a structure in which the impression body-mounting member 20, to which the impression body 5 is directly mounted, can be rotated about three axes like a gyroscope. To be more specific, the three-axis rotating subject jig may include: the jig base 226; an annular frame 233 mounted to the jig base 226; a first rotating frame 232 connected to be rotatable about one axis with respect to the annular frame 233; a second rotating frame 231 connected to be rotatable about one axis with respect to the first rotating frame 232; and the impression body-mounting member 20 connected to be rotatable about one axis with respect to the second rotating frame 231, and configured to fixedly support the impression body 5.

When it is intended to obtain high-precision surface data of the impression body 5 through this configuration, the impression body-mounting member 20 can be rotated in any axial direction between one scan sequence and another scan sequence, and accurate surface data for the impression body 5 can be obtained by performing scan sequences at various angles. Meanwhile, the three-axis rotating subject jig 230 of the embodiment has a mechanical configuration to rotate the subject in any axis direction, as well as about three axes, but may alternatively be configured to rotate the impression body 5 within a limited range with respect to three different axes.

Figure 3:
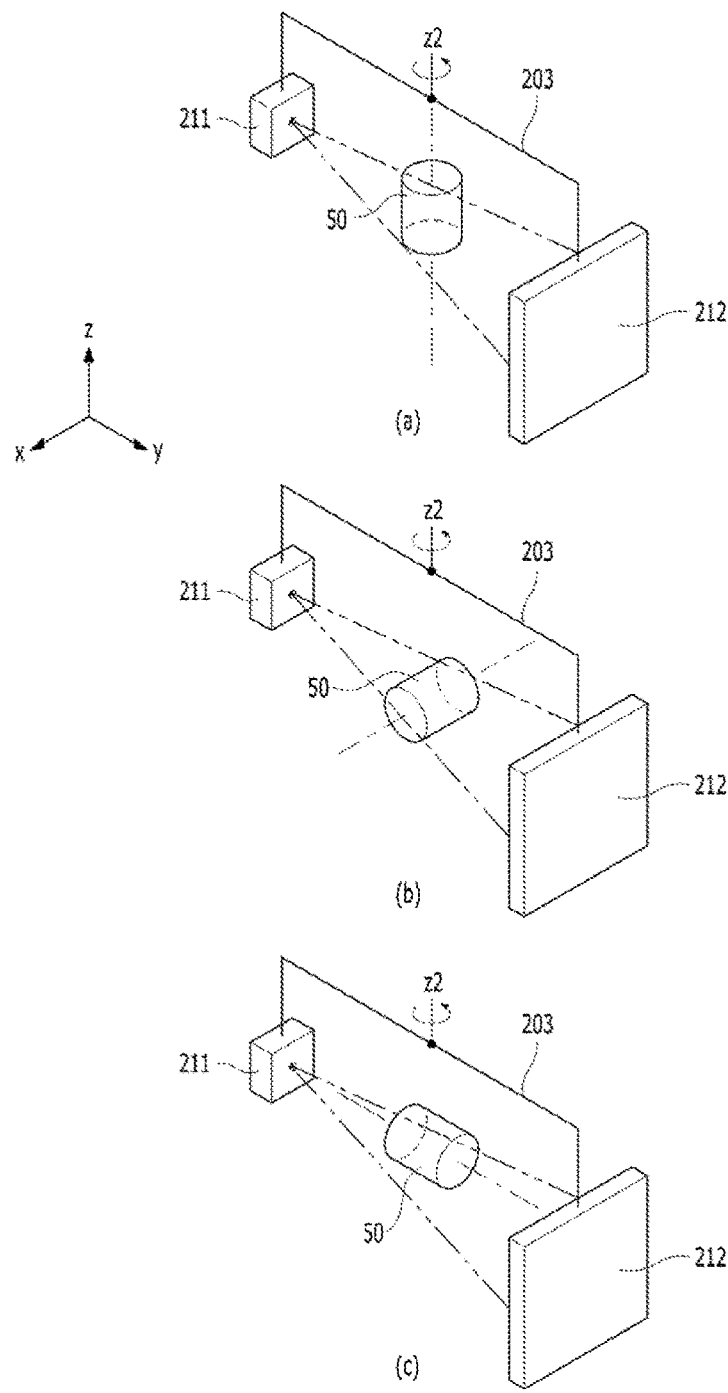
FIG. 3 shows an example of a high-precision X-ray scan involving impression body rotation.

FIG. 3 shows an example of a high-precision X-ray scan involving impression body rotation.

The high-precision X-ray scan according to the embodiment may be achieved by three X-ray scan sequences as shown in FIGS. 3(a), 3(b), and 3(c). The high-precision X-ray scan process may be performed by an X-ray imaging apparatus provided with the three-axis rotating subject jig 230 of FIG. 2. Here, for convenience, description will be made assuming that a subject 50 is arranged in the X-ray propagation path between the X-ray generator 211 and the X-ray sensor 212 disposed at opposite ends of the rotation arm 203, and a single scan sequence is performed while the rotation arm 203 is rotated about the Z2-axis. However, the relative rotation of the X-ray propagation path and the subject 50 may be achieved by rotation of the rotation arm 203 with the subject 50 fixed, as well as by rotation of the subject 50 with the rotation arm 203 fixed.

Firstly, as in (a), in the state where the vertical axis of the subject 50 is fixed in the Z-axis direction, a first scan sequence may be performed by rotating the rotation arm 203, and as in (b) and (c), in the state where the vertical axis of the subject 50 is fixed in X-axis and Y-axis directions, second and third scan sequences may be performed respectively. As described above, by reconstructing a plurality of X-ray imaging data obtained from multiple scan sequences, it is possible to provide three-dimensional surface data as well as CT images more accurate than conventional X-ray CT imaging apparatus. Herein, there is no restriction on the number of times to change the direction of the subject 50, and N scan sequences may be performed with the impression body, subject 50, arranged in N different directions.

Figure 4:
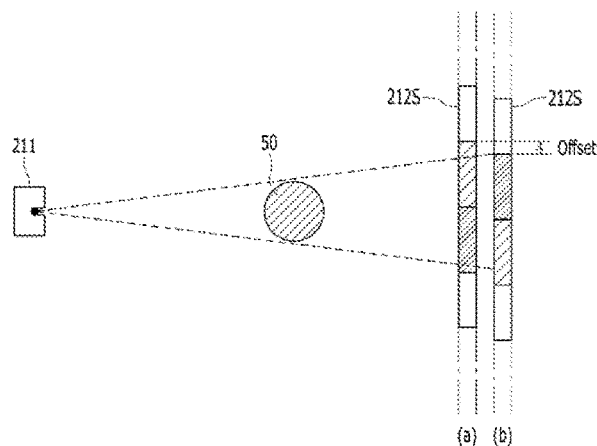
FIG. 4 shows an example of a high-precision X-ray scan involving an X-ray sensor offset.

FIG. 4 shows an example of a high-precision X-ray scan involving an X-ray sensor offset.

As another example of a method of performing a high-precision X-ray scan for a subject such as an impression body to obtain high-precision three-dimensional surface data for the subject, between one X-ray scan sequence and the next X-ray scan sequence, an X-ray sensor 212S may be offset by a distance smaller than a width of one pixel thereof in a direction crossing the X-ray propagation path via the subject 50 from the X-ray generator 211. In the drawing, (a) shows the position of the X-ray sensor 212S in the first scan sequence and (b) shows the position of the X-ray sensor 212S in the second scan sequence. Here, it is preferable that the distances from the X-ray generator 211 and the subject 50 to the X-ray sensor 212S are the same in (a) and (b). By performing the scan sequence several times while offsetting the X-ray sensor by a distance smaller than the width of the pixel, it is possible to provide more accurate CT image and/or three-dimensional surface data for the subject 50.

When the X-ray sensor is offset by 1/M of the width of the pixel for each scan sequence, it is possible to reconstruct high-precision three-dimensional surface data by performing M scan sequences. For example, when four scan sequences are performed while offsetting the X-ray sensor by ¼ of the width of the pixel for each scan sequence, it is possible to achieve the same effect as increasing the resolution of the X-ray sensor four times. In one scan sequence, the direction of the X-ray propagation around the subject 50 may be 360 degrees, but since X-ray imaging is a transmission method unlike the intraoral scanner or impression body scanner, it is possible to acquire imaging data necessary for reconstructing surface data for all directions of the subject with only 180-degree rotation. The rotation range may be selected according to resolution or reconstruction algorithm.

Figure 5:
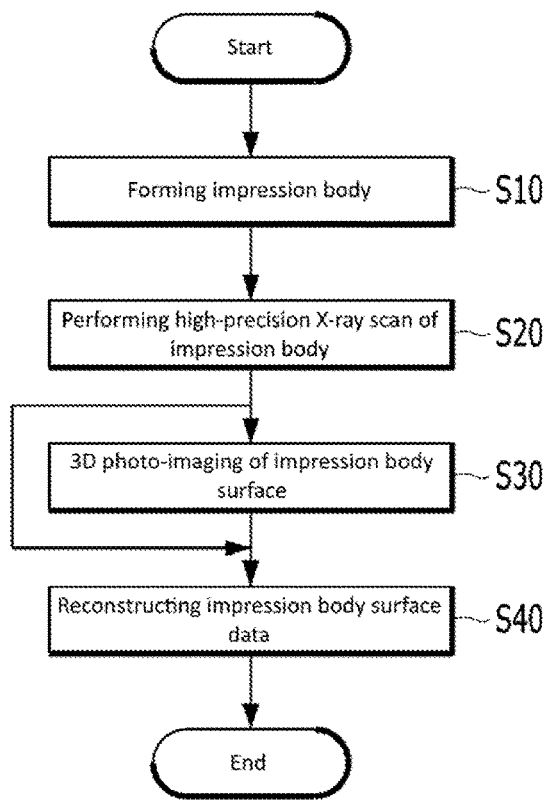
FIG. 5 shows an X-ray imaging method according to an embodiment of the present invention.

FIG. 5 shows an X-ray imaging method according to an embodiment of the present invention.

To provide high-precision surface data of an impression body along with or separately from X-ray CT images for tomographic and/or three-dimensional volumes, the X-ray imaging method according to an aspect of the present invention includes: forming an impression body (s10); performing high-precision X-ray scan of the impression body (s20); and reconstructing impression body surface data (s40). Further, the X-ray imaging method may include 3D photo-imaging of impression body surface (s30) if necessary. The 3D photo-imaging method of the impression body surface and its utilization are as described with reference to the optical camera 213 in FIG. 1.

In the step of forming the impression body (s10), an impression body, such as an engraved or embossed dental model, is formed based on the oral structure of the subject's teeth and gums. Then, the impression body is mounted to the above described impression body-mounting member of the X-ray imaging apparatus, and X-ray imaging is performed. The step of high-precision X-ray scan of the impression body (s20) may be performed in various methods, however, may be typically embodied in two methods as described above.

Figure 6:
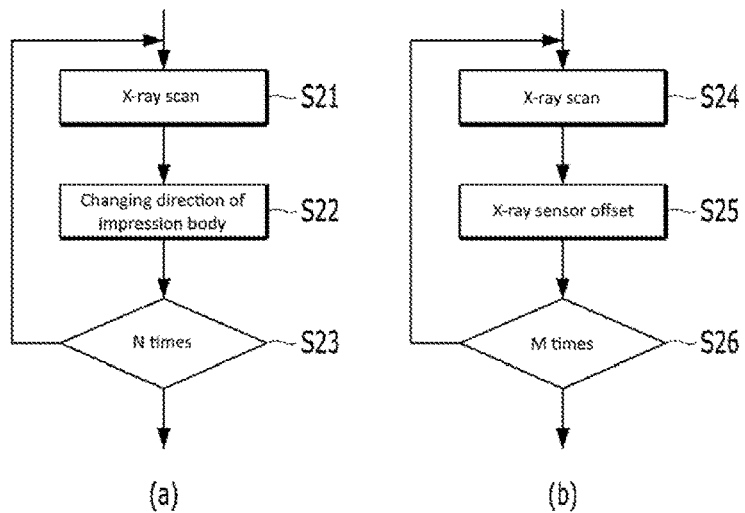
FIG. 6 shows two implementations of the X-ray imaging method according to the embodiment of FIG. 5.

FIG. 6 shows two implementations of the X-ray imaging method according to the embodiment of FIG. 5.

FIG. 6(a) shows a high-precision X-ray imaging method for an impression body, which is the same as described with reference to the X-ray imaging apparatus according to the embodiment of FIG. 3, wherein the method may be configured in such a way that firstly, a scan sequence, as one time X-ray scan, is performed (s21), a direction of the impression body mounted to the impression body-mounting member is changed by operating the subject jig (s22), and the processes is repeated until predetermined N scan sequences are completed (s23). A specific method of performing each process is as described above with reference to FIG. 3.

FIG. 6(b) shows a high-precision X-ray imaging method for an impression body, which is the same as described with reference to the X-ray imaging apparatus according to the embodiment of FIG. 4, wherein the method may be configured in such a way that a scan sequence is performed to X-ray scan the impression body mounted to the subject jig one time (s24), and the X-ray sensor is offset (s25). The offset distance is 1/M (where M is a natural number equal to or greater than 2) of the width of the pixel, and this process may be repeated until the scan sequence of M times is completed (s26). A specific method of performing each process is as described above with reference to FIG. 4.

Figure 7:
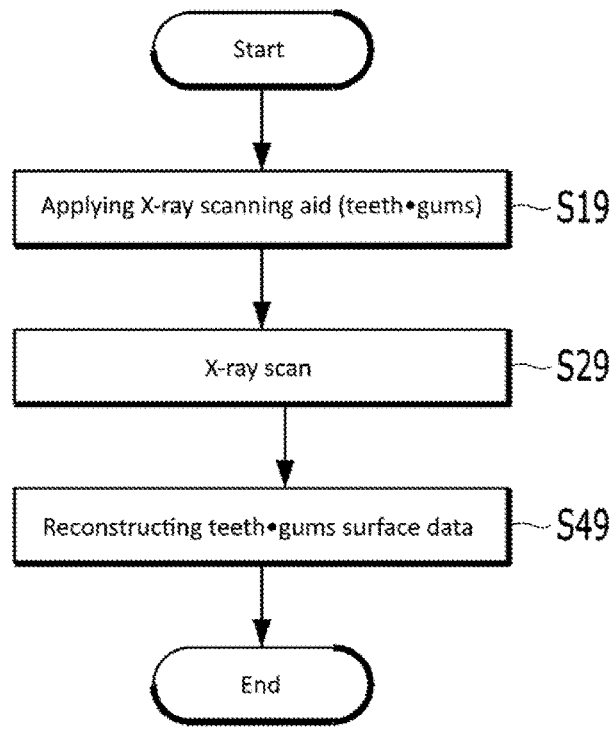
FIG. 7 shows an X-ray imaging method according to an embodiment of the present invention.
Figure 8:
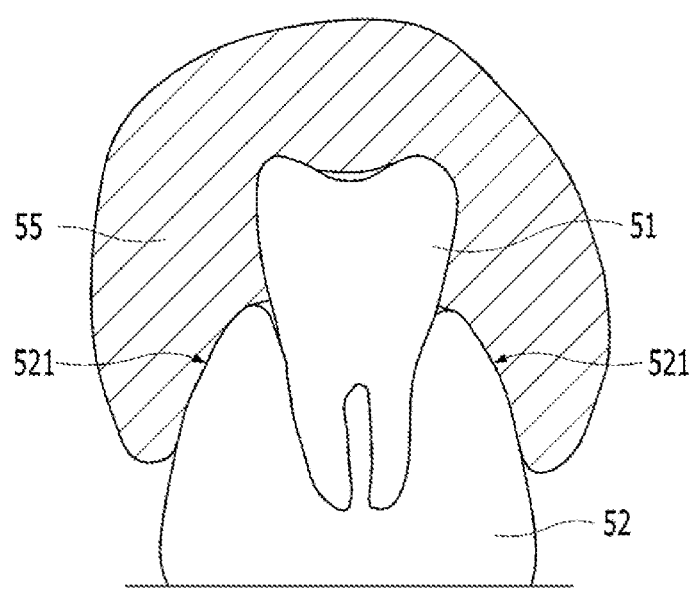
FIG. 8 shows a state where an X-ray scanning aid is applied in the X-ray imaging method according to the embodiment of FIG. 7.

FIG. 7 shows an X-ray imaging method according to an embodiment of the present invention. FIG. 8 shows a state where an X-ray scanning aid is applied in the X-ray imaging method according to the embodiment of FIG. 7.

The X-ray imaging method according to the embodiment relates to a method of providing a CT image and/or three-dimensional surface data including a part of teeth and gums by directly X-ray imaging the oral part of the subject. Firstly, as shown in FIG. 8, an X-ray scanning aid is applied (s19) onto an oral structure of a subject to cover the same, that is, to cover a part of teeth 51 and gums 52. The X-ray scanning aid 55 may be applied to the surface 521 of the oral structure may be applied similar to an impression material to the surface 521 of the oral structure, and it is sufficient that the X-ray scanning aid 55 is able to maintain its shape during a series of X-ray imaging, and it does not need to be molded into a uniform shape as an impression material does.

The X-ray scanning aid 55 may be a soft synthetic resin or may be a liquid or paste-like material having a high viscosity. In particular, the X-ray scanning aid 55 has a CT number different from intraoral materials, such as bones, teeth, soft tissues, forming human teeth, skulls, and gums 52. The CT number is a measure of the degree to which the X-ray is attenuated when they are transmitted through the material during X-ray imaging. The reason why the bone and surrounding tissues can be distinguished from the X-ray images of the human body is that the CT numbers of surrounding tissues such as bones and muscles are different, and the greater the difference between CT numbers, the more accurately the interface can be identified when reconstructing a CT image or three-dimensional surface data. However, in the oral cavity of the human body, the soft tissues of the gums and the mucous membranes inside the oral cavity adjacent to the soft tissues, so it is difficult to identify and reconstruct the interfaces, with which they are in contact, with conventional X-ray imaging methods. According to the embodiment, the X-ray scanning aid is applied therebetween (s19), and the scan sequence is performed to X-ray scan (s29), whereby it is possible to reconstruct teeth and gums surface data with high-precision by using a plurality of X-ray imaging data (s49).

INDUSTRIAL APPLICABILITY

The present invention relates to a dental CT (computed tomography) imaging apparatus and imaging method thereof using X-rays, which is mainly used for dental diagnosis and prosthesis manufacturing, and can be utilized in the field of X-ray diagnostic equipment manufacturing and dental technology field.

The invention claimed is:

1. An X-ray imaging apparatus, comprising:
   an X-ray generator configured to irradiate X-rays;
   an X-ray sensor including a plurality of pixels, the X-ray sensor disposed to face the X-ray generator, and configured to receive X-rays transmitted through a subject to generate an electric signal; and
   a subject jig configured to support the subject and to move the subject to be relatively rotated about at least one axis with respect to an X-ray propagation path between the X-ray generator and the X-ray sensor,
   wherein three-dimensional surface data of the subject is reconstructed by using a plurality of X-ray imaging data acquired through both a first scan sequence in which the subject is relatively rotated about a first axis with respect to the X-ray propagation path, and a second scan sequence in which the X-ray sensor is relatively rotated again about the first axis in a state where the X-ray sensor is offset by a distance smaller than a width of one pixel in a direction crossing the X-ray propagation path.

2. The X-ray imaging apparatus of claim 1, wherein the X-ray sensor is offset by 1/M (where M is a natural number equal to or greater than 2) of the width of the pixel for each scan sequence, and the three-dimensional surface data of the subject is reconstructed by using the plurality of X-ray imaging data acquired through first to Mth scan sequences.

3. An X-ray imaging method, comprising:
   mounting an impression body of an oral structure of a subject to a subject jig having a rotatable impression body-mounting member;
   performing a first scan sequence to relatively rotate the impression body about a first axis with respect to an X-ray propagation path;
   offsetting an X-ray sensor by a distance smaller than a width of one pixel in a direction crossing an X-ray propagation path;
   performing a second scan sequence to relatively rotate the impression body again about the first axis with respect to the X-ray propagation path; and
   reconstructing three-dimensional surface data of the impression body by using a plurality of X-ray imaging data acquired through both the first scan sequence and the second scan sequence.

4. The X-ray imaging method of claim 3, wherein the X-ray sensor is offset by 1/M (where M is a natural number equal to or greater than 2) of the width of the pixel for each scan sequence, and the three-dimensional surface data of the subject is reconstructed by using the plurality of X-ray imaging data acquired through first to Mth scan sequences.

* * * * *